United States Patent
Berno

(10) Patent No.: US 6,584,410 B2
(45) Date of Patent: *Jun. 24, 2003

(54) POLYMORPHISM DETECTION UTILIZING CLUSTERING ANALYSIS

(75) Inventor: Anthony J. Berno, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/764,337

(22) Filed: Jan. 16, 2001

(65) Prior Publication Data

US 2001/0041965 A1 Nov. 15, 2001

Related U.S. Application Data

(63) Continuation of application No. 09/134,758, filed on Aug. 14, 1998, now Pat. No. 6,223,127.
(60) Provisional application No. 60/055,939, filed on Aug. 15, 1997.

(51) Int. Cl.[7] ............. G01N 33/48; C12Q 1/68; C07H 21/04
(52) U.S. Cl. ............ 702/19; 536/23.1; 536/24.3; 536/24.31; 435/6
(58) Field of Search .............. 536/23.1, 24.3, 536/24.31, 22.1; 382/128; 435/6, 5; 430/5, 30; 702/19

(56) References Cited

U.S. PATENT DOCUMENTS

| 5,830,645 | A | 11/1998 | Pinkel et al. ............... 435/6 |
| 5,837,832 | A | 11/1998 | Chee et al. ............... 536/22.1 |
| 6,223,127 | B1 * | 4/2001 | Berno ............... 702/19 |
| 6,228,575 | B1 * | 5/2001 | Gingeras ............... 435/5 |

FOREIGN PATENT DOCUMENTS

| WO | WO 95/11995 | 5/1995 |
| WO | 97/14958 | 4/1997 |
| WO | WO 97/29212 | 8/1997 |
| WO | 97/29212 | 8/1997 |
| WO | WO 97/27317 | 7/1999 |

OTHER PUBLICATIONS

Michaels, George S. et al., "Cluster Analysis and Data Visualization of Large–Scale Gene Expression Data", George Mason University, Fairfax, VA 1997, p. 42–52.

Ermolaeva et al., "Data management and analysis for gene expression arrays," Sep. 1998, Nature Genetics, vol. 20, pp. 19–23.

Mark Schena, "Genome analysis with gene expression microarrays," 1996, BioEssays, vol. 18, No. 5, pp. 427–431.

Mark Schena et al., "Parallel human genome analysis: Microarray–based expression," Oct. 1996, Proc. Natl. Acad. Sci., USA, vol. 93, pp. 10614–10619.

R. J. Lipschutz et al., "Using oligonucleotide Probe Arrays to Access Genetic Diversity," 1995, BioTechniques, vol. 19, No. 3, pp. 442–447.

Michael Palmer, Ordination Methods for ecologist, A Glossary of Ordination–Related Terms, Oklahoma State University, Botany Department. Internet address: http//:www.okstate.edu/artsci/botany/ordinate/glossary.htm.

* cited by examiner

Primary Examiner—Sean McGarry
Assistant Examiner—Janet L. Epps-Ford
(74) Attorney, Agent, or Firm—Ritter, Lang & Kaplan LLP

(57) ABSTRACT

Systems and methods for detecting differences in sample polymers, such as nucleic acid sequences, are provided. Hybridization affinity information for the sample polymers is clustered so that the differences, if any, between or among the sample polymers can be readily identified. By clustering the hybridization affinity information of the sample polymers, differences in the sample polymers can be accurately achieved even in the presence of random and systematic errors.

42 Claims, 10 Drawing Sheets

POLYMORPHISM DETECTION UTILIZING CLUSTERING ANALYSIS

This application claims the benefit of U.S. Provisional Application No. 60/055,939, filed Aug. 15, 1997, and is a continuation of U.S. patent application Ser. No. 09/134,758, filed Aug. 14, 1998, now issued as U.S. Pat. No. 6,223,127, both of which are hereby incorporated by reference.

BACKGROUND OF THE INVENTION

The present invention relates to detecting differences in polymers. More specifically, the present invention relates to detecting polymorphisms in sample nucleic acid sequences by clustering hybridization affinity information.

Devices and computer systems for forming and using arrays of materials on a chip or substrate are known. For example, PCT applications WO92/10588 and 95/11995, both incorporated herein by reference for all purposes, describe techniques for sequencing or sequence checking nucleic acids and other materials. Arrays for performing these operations may be formed according to the methods of, for example, the pioneering techniques disclosed in U.S. Pat. Nos. 5,445,934, 5,384,261 and 5,571,639, each incorporated herein by reference for all purposes.

According to one aspect of the techniques described therein, an array of nucleic acid probes is fabricated at known locations on a chip. A labeled nucleic acid is then brought into contact with the chip and a scanner generates an image file indicating the locations where the labeled nucleic acids are bound to the chip. Based upon the image file and identities of the probes at specific locations, it becomes possible to extract information such as the nucleotide or monomer sequence of DNA or RNA. Such systems have been used to form, for example, arrays of DNA that may be used to study and detect mutations relevant to genetic diseases, cancers, infectious diseases, HIV, and other genetic characteristics.

The VLSIPS™ technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. The oligonucleotide probes on the DNA probe array are used to detect complementary nucleic acid sequences in a sample nucleic acid of interest (the "target" nucleic acid).

For sequence checking applications, the chip may be tiled for a specific target nucleic acid sequence. As an example, the chip may contain probes that are perfectly complementary to the target sequence and probes that differ from the target sequence by a single base mismatch. For de novo sequencing applications, the chip may include all the possible probes of a specific length. The probes are tiled on a chip in rows and columns of cells, where each cell includes multiple copies of a particular probe. Additionally, "blank" cells may be present on the chip which do not include any probes. As the blank cells contain no probes, labeled targets should not bind specifically to the chip in this area. Thus, a blank cell provides a measure of the background intensity.

The interpretation of hybridization data from hybridized chips can encounter several difficulties. Random errors, such as physical defects on the chip, can cause individual probes or spatially related groups of probes exhibit abnormal hybridization (e.g., by abnormal fluorescence). Systematic errors, such as the formation of secondary structures in the probes or the target, can also cause reproducible, but still misleading hybridization data.

For many applications, it is desirable to determine if there are differences between and among sample nucleic acid sequences, such as polymorphisms at a base position. It would be desirable to have systems and methods of detecting these differences in a way that is not overly affected by random and systematic errors.

SUMMARY OF THE INVENTION

The present invention provides innovative systems and methods for detecting differences in sample polymers, such as nucleic acid sequences. Hybridization affinity information for the sample polymers is clustered so that the differences, if any, between or among the sample polymers can be readily identified. By clustering the hybridization affinity information of the sample polymers, differences in the sample polymers can be accurately achieved even in the presence of random and systematic errors. Additionally, polymorphisms can be detected in sample nucleic acids regardless of what basecalling has reported. Several embodiments of the invention are described below.

In one embodiment, the invention provides a method of detecting differences in sample polymers. Multiple sets of hybridization affinity information are input, where each set of hybridization affinity information includes hybridization affinities between a sample polymer and polymer probes. The multiple sets of hybridization affinity information are clustered into multiple clusters such that all sets of hybridization affinity information in each cluster are more similar to each other than to the sets of hybridization affinity information in another cluster. The multiple clusters can then be analyzed to detect if there are differences in the sample polymers. For example, if the multiple clusters do not form clusters where subclusters are very similar yet very different from other clusters, this can indicate that the sample polymers are the same. Otherwise, the sample polymers can be different.

In another embodiment, the invention provides a method of detecting polymorphisms in sample nucleic acid sequences. Multiple sets of hybridization affinity information are input, where each set of hybridization affinity information includes hybridization affinities between a sample nucleic acid sequence and nucleic acid probes. The multiple sets of hybridization affinity information are hierarchically clustered into a plurality of clusters such that all sets of hybridization affinity information in each cluster are more similar to each other than to the sets of hybridization affinity information in another cluster. The multiple clusters can then be analyzed to detect if there are polymorphisms in the sample polymers. The polymorphisms can include mutations, insertions and deletions.

Other features and advantages of the invention will become readily apparent upon review of the following detailed description in association with the accompanying drawings.

DETAILED DESCRIPTION OF PREFERRED EMBODIMENTS

In the description that follows, the present invention will be described in reference to preferred embodiments that utilize VLSIPS™ technology for making very large arrays of oligonucleotide probes on chips. However, the invention is not limited to nucleic acids or to this technology and may be advantageously applied to other polymers and manufacturing processes. Therefore, the description of the embodiments that follows for purposes of illustration and not limitation.

Figure 1:
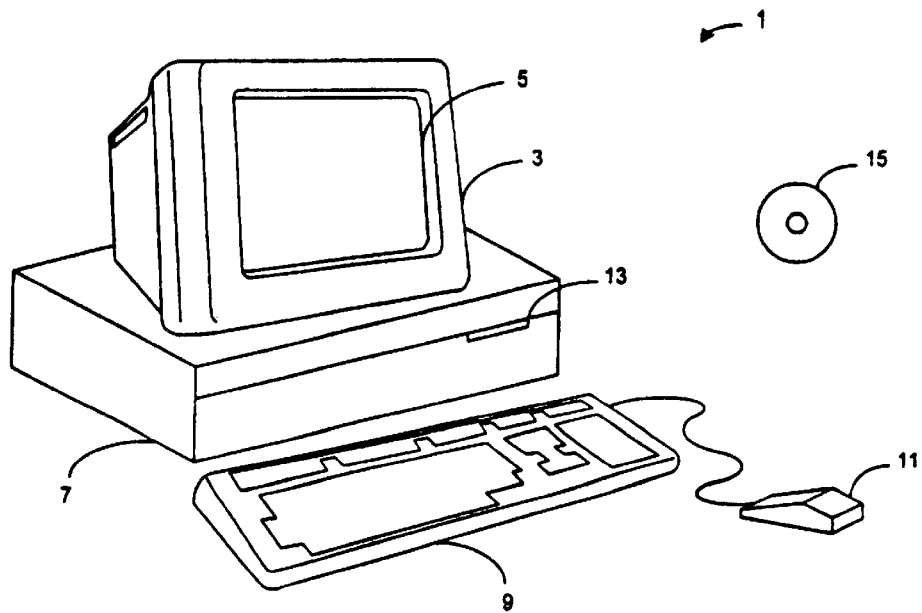
FIG. 1 illustrates an example of a computer system that may be utilized to execute the software of an embodiment of the invention.

FIG. 1 illustrates an example of a computer system that may be used to execute the software of an embodiment of the invention. FIG. 1 shows a computer system 1 that includes a display 3, screen 5, cabinet 7, keyboard 9, and mouse 11. Mouse 11 may have one or more buttons for interacting with a graphical user interface. Cabinet 7 houses a CD-ROM drive 13, system memory and a hard drive (see FIG. 2) which may be utilized to store and retrieve software programs incorporating computer code that implements the invention, data for use with the invention, and the like. Although a CD-ROM 15 is shown as an exemplary computer readable storage medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
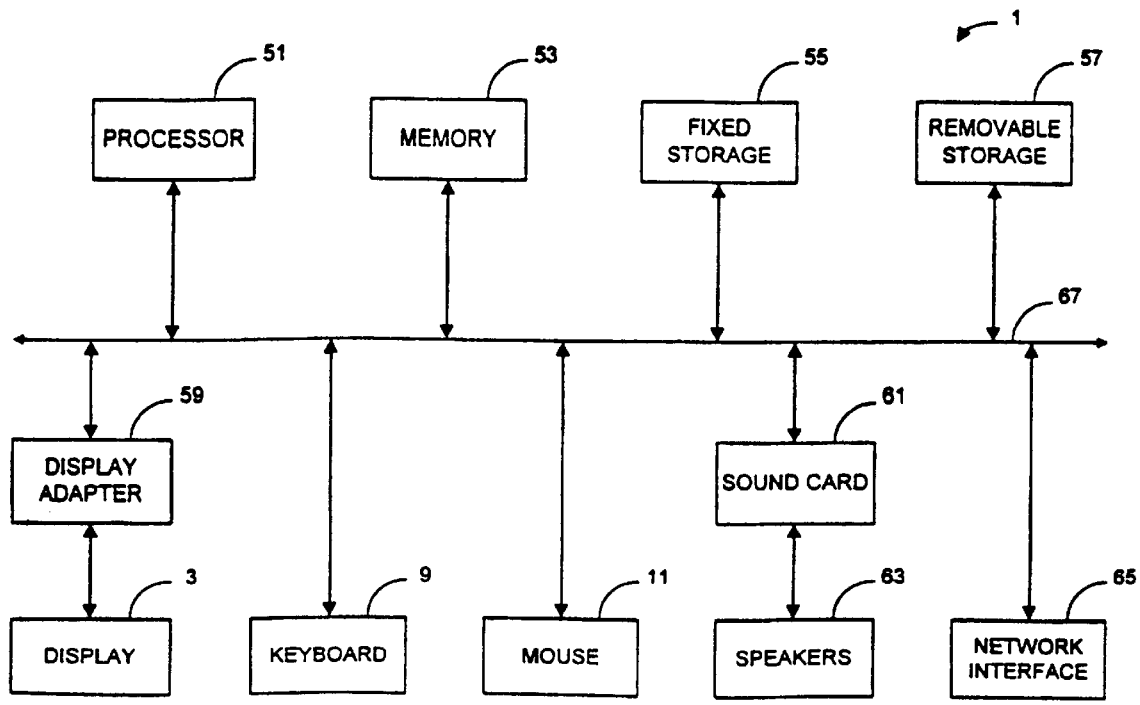
FIG. 2 illustrates a system block diagram of the computer system of FIG. 1.

FIG. 2 shows a system block diagram of computer system 1 used to execute the software of an embodiment of the invention. As in FIG. 1, computer system 1 includes monitor 3 and keyboard 9, and mouse 11. Computer system 1 further includes subsystems such as a central processor 51, system memory 53, fixed storage 55 (e.g., hard drive), removable storage 57 (e.g., CD-ROM drive), display adapter 59, sound card 61, speakers 63, and network interface 65. Other computer systems suitable for use with the invention may include additional or fewer subsystems. For example, another computer system could include more than one processor 51 (i.e., a multi-processor system) or a cache memory.

The system bus architecture of computer system 1 is represented by arrows 67. However, these arrows are illustrative of any interconnection scheme serving to link the subsystems. For example, a local bus could be utilized to connect the central processor to the system memory and display adapter. Computer system 1 shown in FIG. 2 is but an example of a computer system suitable for use with the invention. Other computer architectures having different configurations of subsystems may also be utilized.

For purposes of illustration, the present invention is described as being part of a computer system that designs a chip mask, synthesizes the probes on the chip, labels the nucleic acids, and scans the hybridized nucleic acid probes. Such a system is fully described in U.S. Pat. No. 5,571,639 that has been incorporated by reference for all purposes. However, the present invention may be used separately from the overall system for analyzing data generated by such systems.

Figure 3:
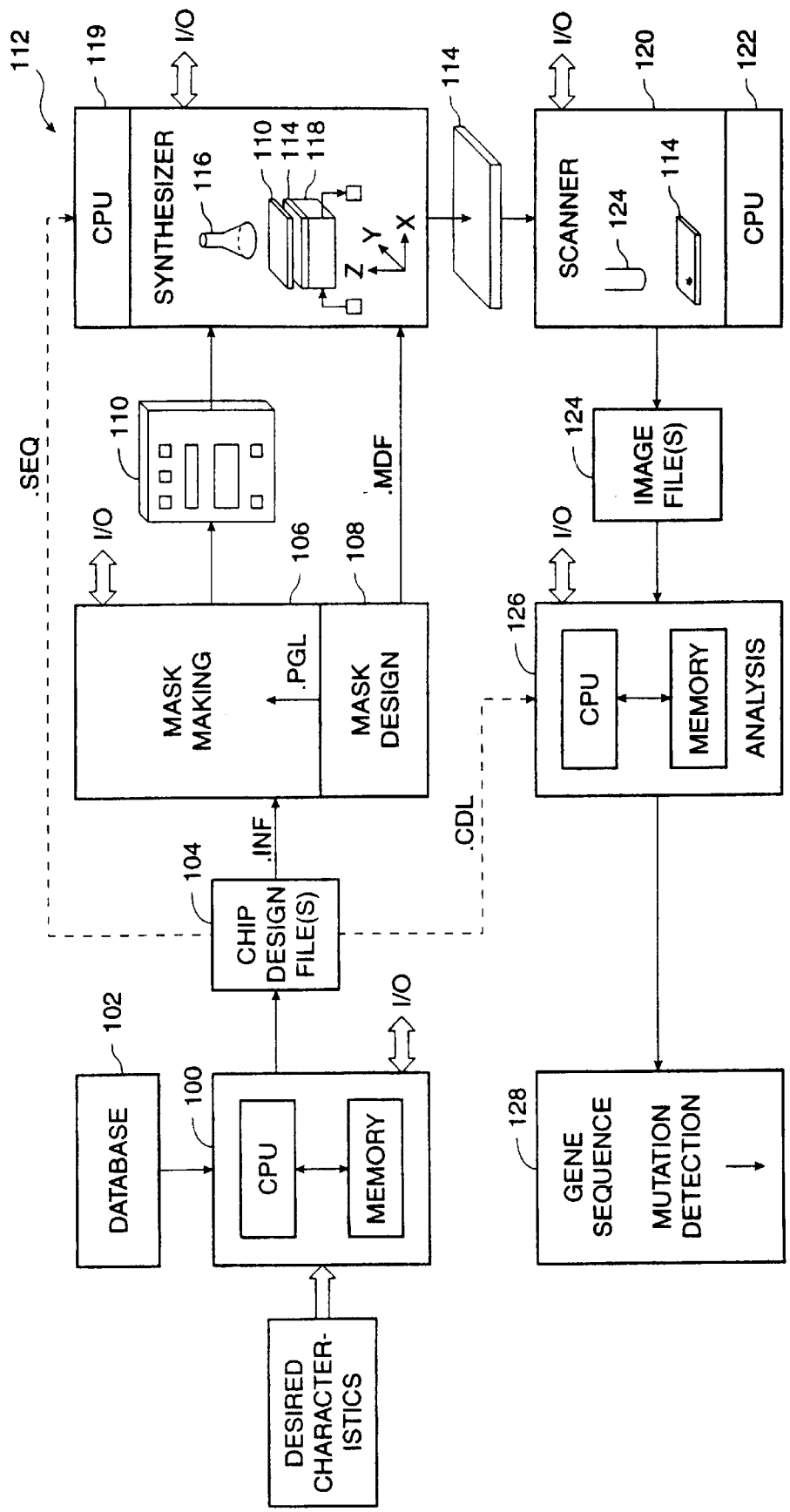
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA and DNA. The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical regents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in scanning system 120. Although preferred embodiments utilize fluorescent markers, other markers may be utilized that provide differences in radioactive intensity, light scattering, refractive index, conductivity, electroluminescence, or other large molecule detection data. Therefore, the present invention is not limited to analyzing fluorescence measurements of hybridization but may be readily utilized to analyze other measurements of hybridization.

Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers (e.g., DNA probes on the substrate), and since the monomer sequence of the polymers on the substrate is known as a function of position, it becomes possible to determine the sequence(s) of polymer(s) on the substrate that are complementary to the target.

The image file 124 is provided as input to an analysis system 126 that incorporates the synthesis integrity evaluation techniques of the present invention. Again, the analysis system may be any one of a wide variety of computer system(s), but in a preferred embodiment the analysis system is based on a WINDOWS NT workstation or equivalent. The analysis system may analyze the image file(s) to generate appropriate output 128, such as the identity of specific mutations in a target such as DNA or RNA.

Figure 4:
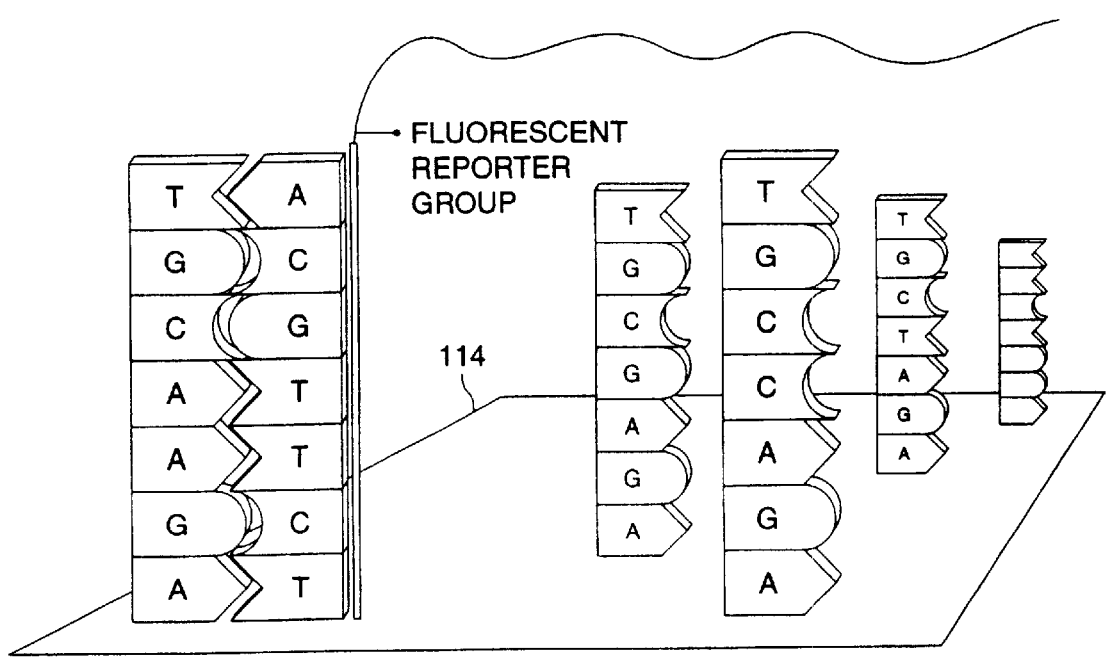
FIG. 4 illustrates conceptually the binding of probes on chips.

FIG. 4 illustrates the binding of a particular target DNA to an array of DNA probes 114. As shown in this simple example, the following probes are formed in the array:

3'-AGAACGT
      AGACCGT
      AGAGCGT
      AGATCGT
      •
      •
      •

As shown, when the fluorescein-labeled (or otherwise marked) target 5'-TCTTGCA is exposed to the array, it is complementary only to the probe 3'-AGAACGT, and fluorescein will be primarily found on the surface of the chip where 3'-AGAACGT is located. The chip contains cells that include multiple copies of a particular probe and the cells may be square regions on the chip.

Figure 5:
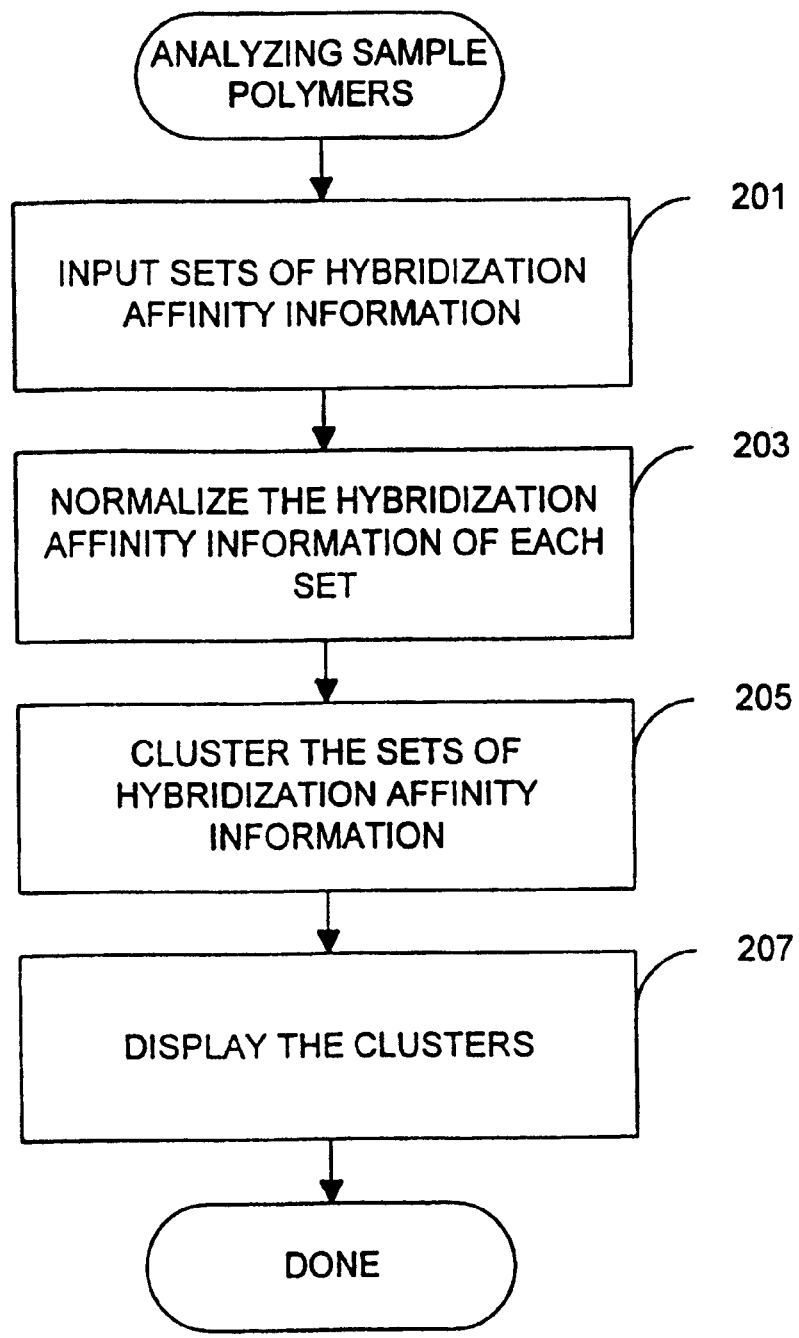
FIG. 5 shows a high level flowchart of a process of analyzing sample polymers.

FIG. 5 is a high level flowchart of a process of analyzing sample polymers, such as nucleic acid sequences. At a step 201, sets of hybridization affinity information are input to a computer system. The hybridization affinity information can be in any number of forms including fluorescent, radioactive or other data. The hybridization affinity information can be utilized without modification as input for clustering analysis. However, the variations in the data can be reduced by normalizing the data.

The hybridization affinity information of each set is normalized at a step 203. Normalization can be utilized to provide more consistent data between and within experiments. As an example, normalization can include dividing each hybridization affinity value by the sum of all the other hybridization affinity values, thus reducing each hybridization affinity value to a value between 0 and 1. Although normalization can be beneficial in some applications, it is not required. Therefore, the steps shown in the flowcharts illustrate specific embodiments and steps can be deleted, inserted, combined, and modified within the spirit and scope of the invention.

At a step 205, the sets of hybridization affinity information are clustered. Clustering analysis processes typically accept as input multiple patterns of data (e.g., represented by vectors of floating point numbers) and rearrange the patterns into clusters of similar patterns. Preferred embodiments arrange patterns of data into hierarchical clusters where each cluster includes clusters that are more similar to each other than to other clusters.

Once the clusters are formed, they can be displayed on the screen for a user to analyze at a step 207. In addition to displaying the clusters, the computer system can also interpret the clusters and output to the user the number of distinct clusters that were found. The description of FIG. 5 has been provided at a high level to give the reader an initial understanding of the invention and the description that follows will describe the invention in more detail.

Figure 6:
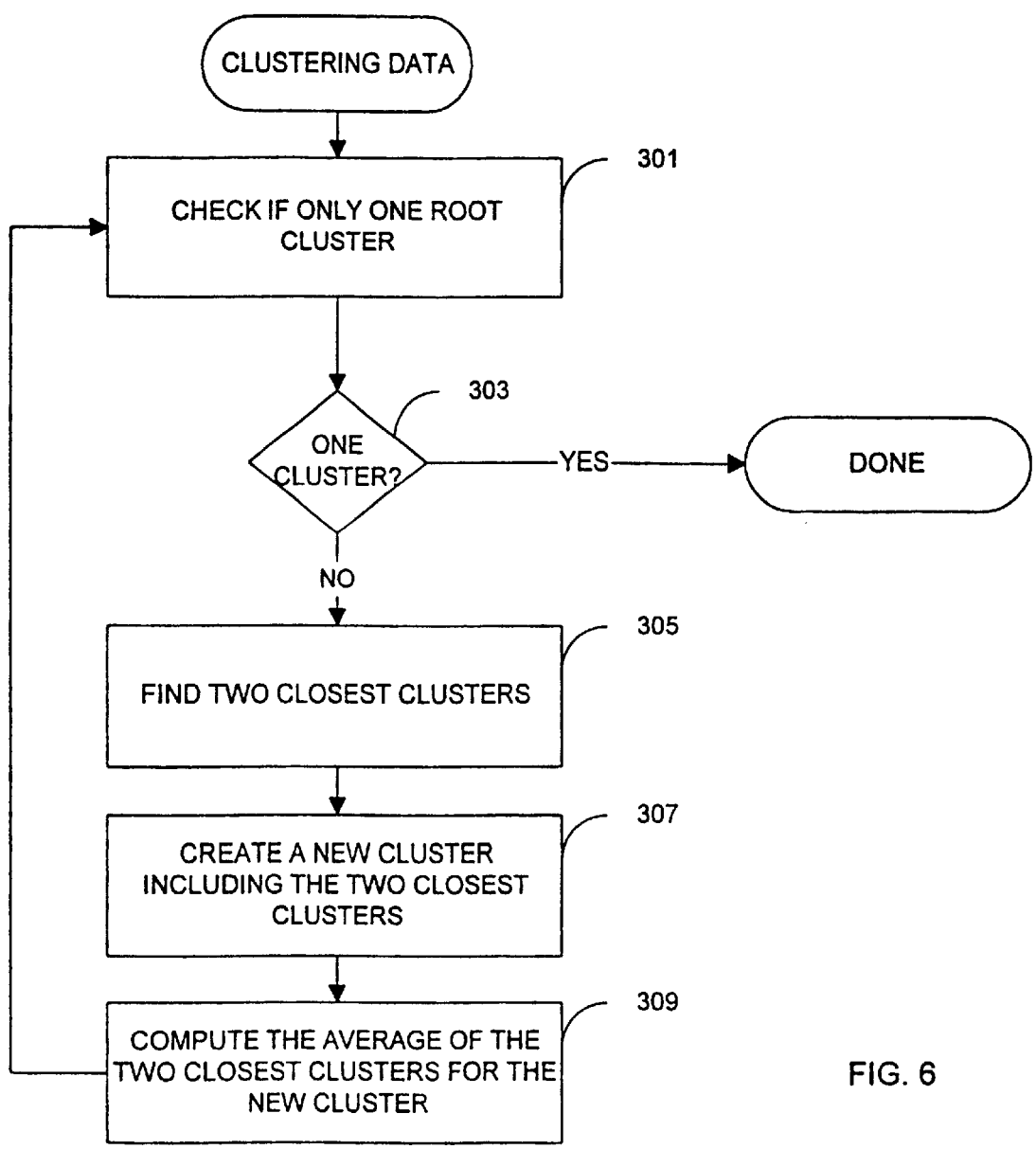
FIG. 6 shows a flowchart of a process clustering hybridization affinity data.

FIG. 6 shows a flowchart of a process clustering hybridization affinity data. At a step 301, a check is performed to see if the sets of hybridization affinity information have been clustered into a single root cluster. A cluster can include one or more subclusters and a root cluster is a cluster that is not included in any other cluster. In the description that follows, a cluster (or subcluster) can be a single set of hybridization affinity information or include multiple sets.

Initially, each set of hybridization affinity information is considered a single cluster. As the clustering continues, clusters that are found to be similar enough are grouped together into a new cluster. When it is determined that all the sets of hybridization affinity information are clustered into a single root cluster at a step 303, the clustering is done.

Otherwise, the two closest clusters are found at a step 305. By being closest, it is meant that a metric indicates that two of the clusters include data that are more similar to each other than any of the other clusters are to another cluster. Any number of different metrics can be utilized including the Euclidean distance described in more detail in reference to FIG. 7. Most preferably, the metric satisfies the triangle inequality such that $f(a,c)<=f(a,b)+f(b,c)$ for any set of data patterns $\{a,b,c\}$.

In the embodiments described herein, a cluster includes up to two sets of hybridization affinity information. However, there is no requirement that the clusters be limited in this manner. For example, the invention can be advantageously applied to clusters that can include up to three or more sets of hybridization affinity information by an extension of the principles described herein.

At a step 307, a new cluster is created that includes the two closest clusters. In order to compare the new cluster with other clusters, a value should be calculated to represent the data in the new cluster. In one embodiment, the average of the two closest clusters is computed for the new cluster at a step 309. After the new cluster has been created, the flow proceeds to step 301 to check if only one root cluster remains.

Figure 7:
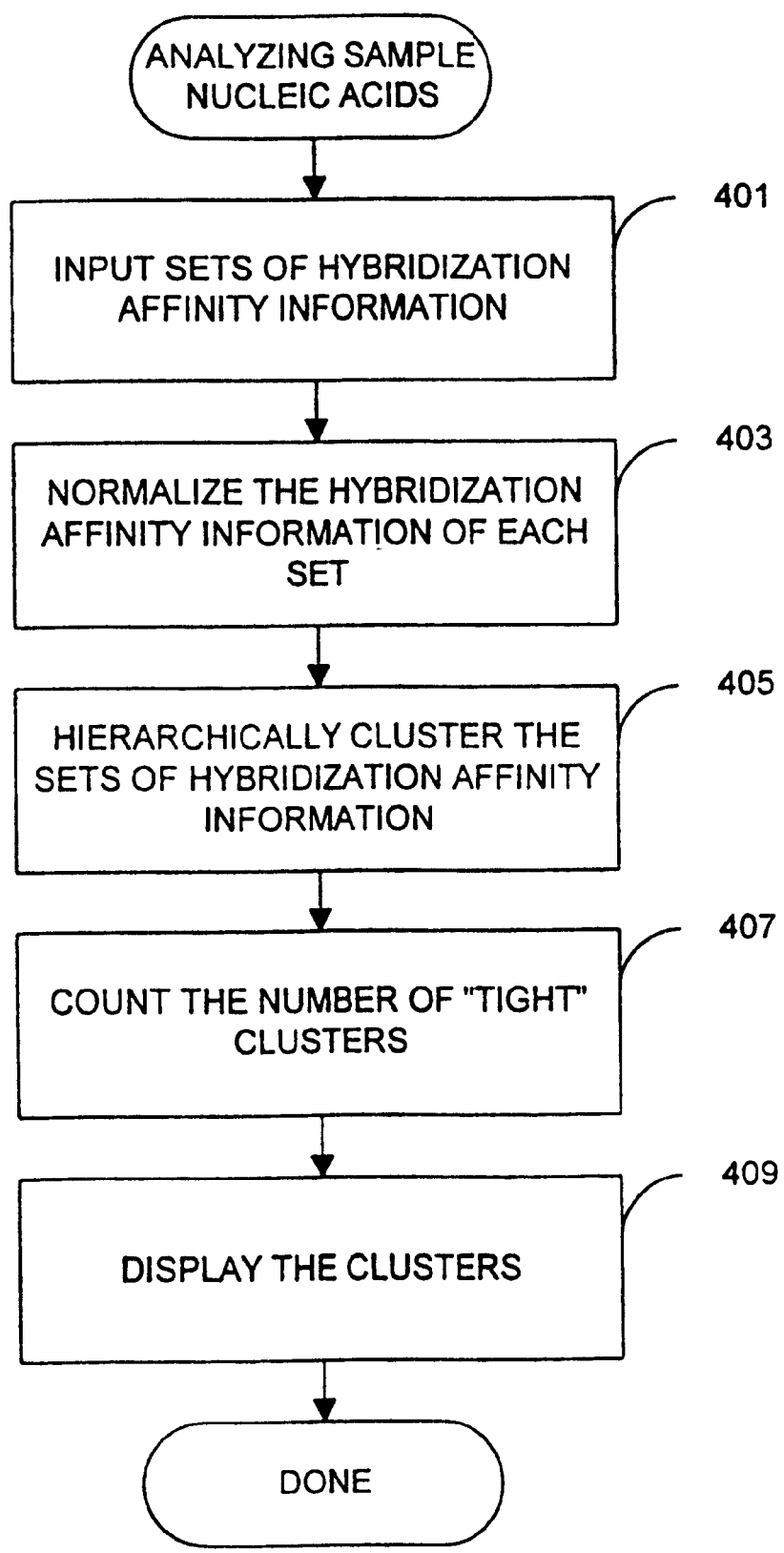
FIG. 7 shows a flowchart of a process of analyzing sample nucleic acid sequences.

FIG. 7 shows a flowchart of a process of analyzing sample nucleic acid sequences. For this embodiment, hybridization data from a chip with both sense and anti-sense probes are utilized. Fragments from the sense and anti-sense strands of a target are labeled and exposed to the chip resulting in four hybridization affinity measurements for the sense strand and four hybridization affinity measurements for the anti-sense strand at each interrogation position.

As an example, if the sense strand of a target sequence (or portion thereof) is 5'-GTAACGTTG then the following sense probes would interrogate the underlined base position:

3'-TTACA
3'-TTCCA
3'-TTGCA
3'-TTTCA

The anti-sense strand of the target sequence (or portion thereof) would be 3'-CATTGCAAC and the following sense probes would interrogate the underlined base position for the anti-sense strand:

5'-AAAGT
5'-AACGT
5'-AAGGT
5'-AATGT

Accordingly, in this embodiment, there are eight hybridization affinities, one for each probe, for each interrogation position.

At a step 401, sets of hybridization affinity information are input to a computer system. This can include reading a file that includes hybridization affinity data for each base position that is interrogated in the target. As discussed above, the hybridization affinity data for a base position can include eight measured hybridization affinities. The eight measured hybridization affinities can be stored as a set or pattern of eight values (e.g., photon counts) such as $\{A_1, A_2, \ldots, A_8\}$.

The hybridization affinity information of each set is normalized at a step 403. Normalizing the hybridization affinity information can de-emphasize differences that are not directly related to target sequence composition. One effective strategy for normalizing the hybridization affinities of a set is to first calculate the average of the hybridization affinities for a set and subtract this average from each hybridization affinity in the set. Then, each average-subtracted hybridization affinity is divided by the square root of the sum of squares of the hybridization affinities of the set minus the average hybridization affinity. In other words, the following formula is utilized normalize each hybridization affinity of a set:

$$A_I = (A_I - \bar{A})/\text{square root}((A_1 - \bar{A})^2 + (A_2 - \bar{A})^2 + \ldots + (A_8 - \bar{A})^2)$$

where I is from 1 to 8 and A is the average of $A_1, A_2, \ldots, A_8$.

Figure 8:
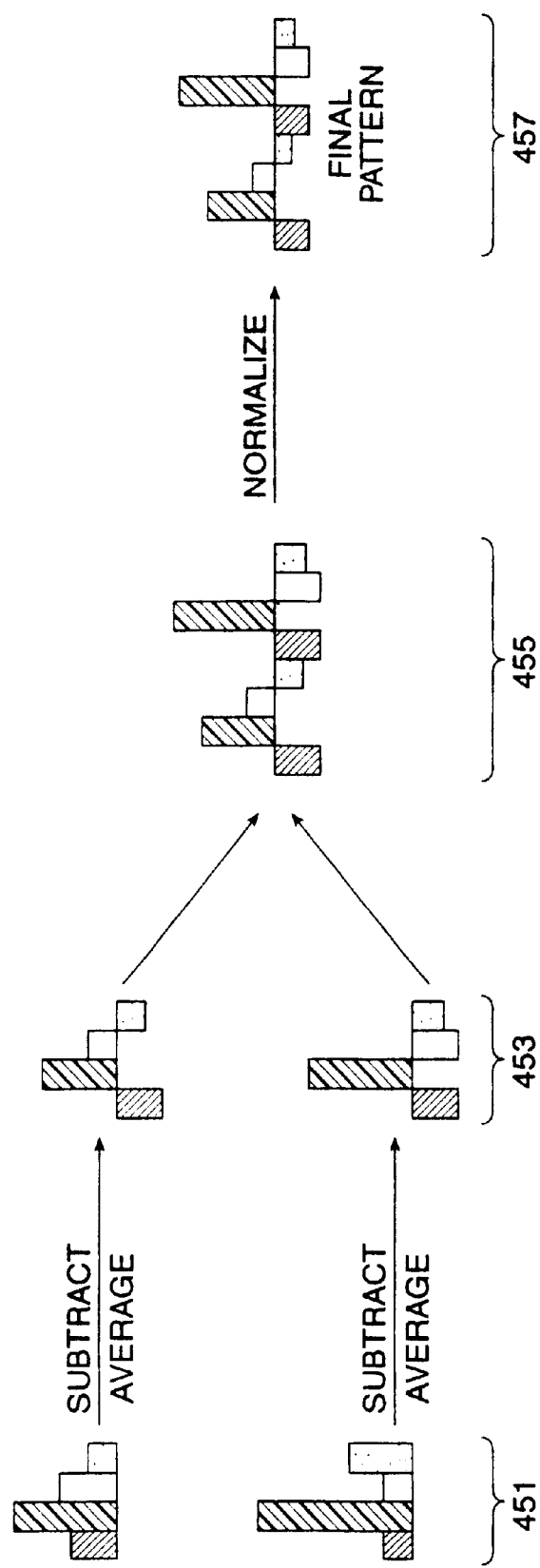
FIG. 8 shows graphically how normalization can affect the hybridization affinities.

FIG. 8 shows graphically how the normalization can affect the hybridization affinities. Hybridization affinities 451 are the raw data measured from the chip and the height of the bars indicates the relative measured hybridization affinity.

Average-subtracted hybridization affinities 453 show that the hybridization affinities are now vectors in two possible directions. The average-subtracted hybridization affinities are combined into an intermediate vector pattern 455. Normalization of vector pattern 455 is completed by dividing each vector by the denominator above to produce a final normalized vector pattern 457.

Normalization can correct for varying backgrounds and overall hybridization affinity values, while preserving the rank of each hybridization affinity within the set as well as the difference in overall hybridization affinity between the sense and anti-sense probes. Additionally, by normalizing the set of eight values in the manner described, the distance between any two patterns is bounded by (0, 2), thus offering a consistent scale on which to pattern differences can be evaluated.

Returning to FIG. 7, at a step 405, the sets of hybridization affinity information are hierarchically clustered. Any number of clustering algorithms can be utilized. In preferred embodiments, a modification of the mean linkage clustering algorithm is utilized. The value of a cluster that includes only a single set of hybridization affinities is the pattern of eight hybridization affinities. The value of a cluster C that includes two clusters A and B is as follows:

$$C_I = \text{average}(A_I, B_I)$$

where I is from 1 to 8. Thus, each cluster is represented by an eight value pattern. Other linkage calculations can be utilized including traditional mean linkage wherein the mean of the distances between each member of a pattern is utilized. Additionally, the greatest (or least) distance between two members of two clusters can be utilized as the linkage formula.

The distance between two clusters is typically determined by a distance metric. Many different distance metrics can be utilized including the Euclidean distance, city-block distance, correlation distance, angular distance, and the like. Most preferably, the Euclidean distance is utilized and it is calculated as follows:

$$D_{AB} = \text{square root}((A_1 - B_1)^2 + (A_2 - B_2)^2 + \ldots + (A_8 - B_8)^2)$$

where I is from 1 to 8. The city-block distance can be calculated as follows:

$$D_{AB} = |(A_1 B_1)| + |(A_2 - B_2)| + \ldots + |(A_8 - B_8)|$$

where I is from 1 to 8 and |X| represents the absolute value of X.

At a step 407, the number of "tight" clusters is counted. A "tight" cluster is a defined as any cluster where the average distance from the cluster mean to the means of its subclusters is less than the distance to its nearest sibling cluster by a similarity factor (e.g., a factor of 3). It is fairly easy for a user to visually identify clusters, but the number of tight clusters can be utilized as a calculated determination of the number of clusters. If there are two or more tight clusters, the interrogation position is likely to be polymorphic. It should be noted that increasing the number of dimensions in an input pattern strongly reduces the probability that two patterns will be similar by chance and the value of the similarity factor can be adjusted accordingly.

The clusters are displayed at a step 409. The clusters can be displayed any number of ways, but in preferred embodiments, they are displayed as dendrograms. Dendrograms are diagrams that represent the clusters. The distance between the clusters can be represented on the dendrogram so that the user can more readily identify the clusters that would be indicative of a polymorphism such as a mutation, insertion or deletion. In other words, the distance between the clusters varies with the similarity of the clusters.

Figure 9:
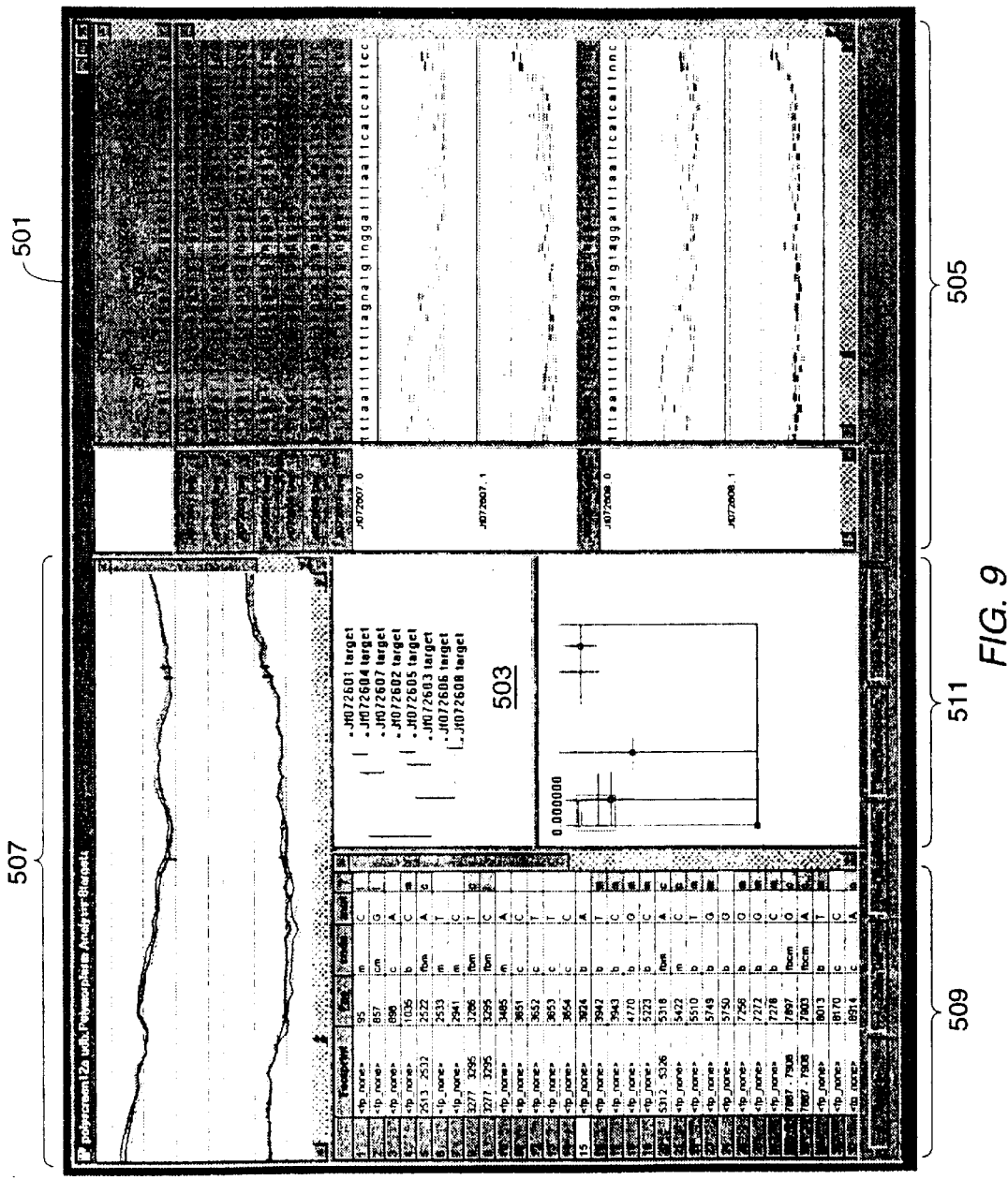
FIG. 9 illustrates a screen display including a dendrogram indicating that there does not appear to be a polymorphism at the base position of interest (SEQ ID NO:1; SEQ ID NO:2; SEQ ID NO:3; SEQ ID NO:4; SEQ ID NO:5; and SEQ ID NO:6).

As an example, FIG. 9 illustrates a screen display including a dendrogram indicating that there does not appear to be a polymorphism at the base position of interest. A screen display 501 includes a dendrogram 503. The dendrogram will be described in more detail in reference to FIG. 10.

Screen display 501 includes raw data 505 and the indicated base calls. A plot 507 of hybridization affinities vs. base position is shown for both the sense and anti-sense strands for pattern recognition. A table 509 includes information on base positions for the chip. Additionally, an image 511 provides information for mutant fraction estimation. Dendrogram 503 (and others) will be the focus of the following paragraphs.

Figure 10:
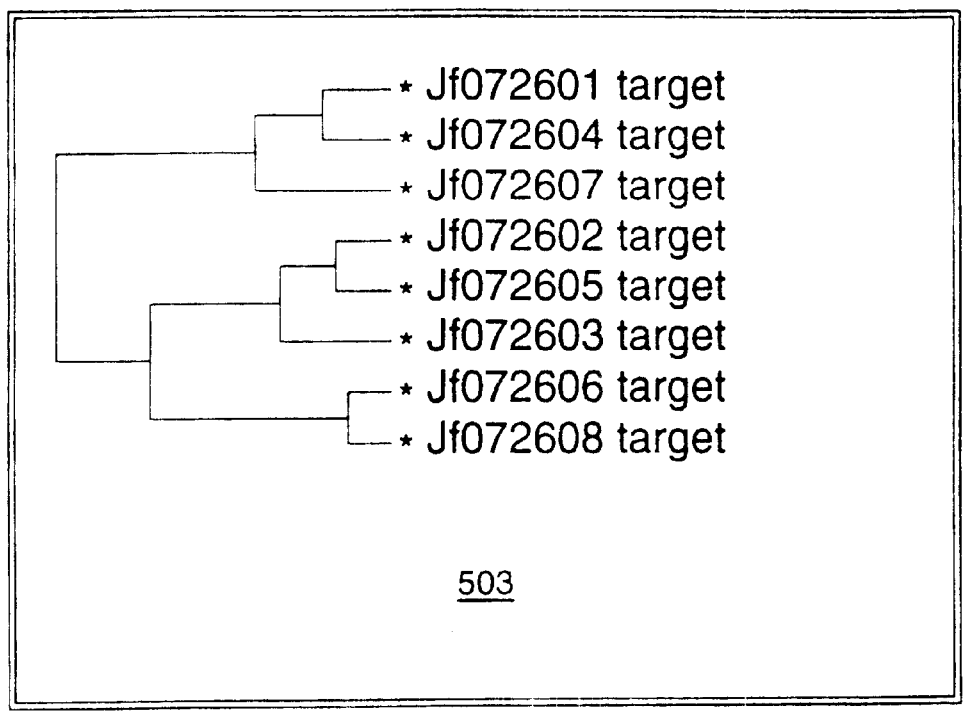
FIG. 10 shows the dendrogram of FIG. 9.

FIG. 10 shows a dendrogram from FIG. 9 that clusters eight sets of hybridization affinity information (represented by the target name). A visual inspection of dendrogram 503 reveals that the distance between the clusters (illustrated by the horizontal lengths of the dendrogram) are relatively constant. This indicates that the patterns are relatively constant and therefore, it does not appear likely there is a polymorphism at the interrogation position.

Figure 11:
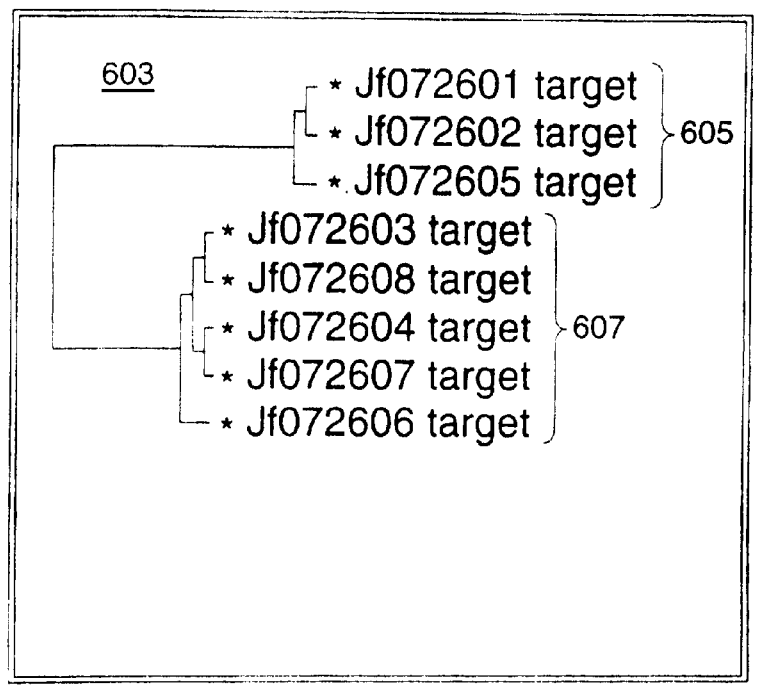
FIG. 11 illustrates a dendrogram indicating that is likely a polymorphism at the base position of interest.

FIG. 11 illustrates a dendrogram indicating that is likely a polymorphism at the base position of interest. Dendrogram 603 shows the clustering of eight sets of hybridization affinity information. A visual inspection of the dendrogram reveals that there appears to be two clusters 605 and 607 where the distance between members of one cluster is much less than the distance between members of other clusters. As the patterns fall in two clusters, there is likely a polymorphism at the interrogation position.

Figure 12:
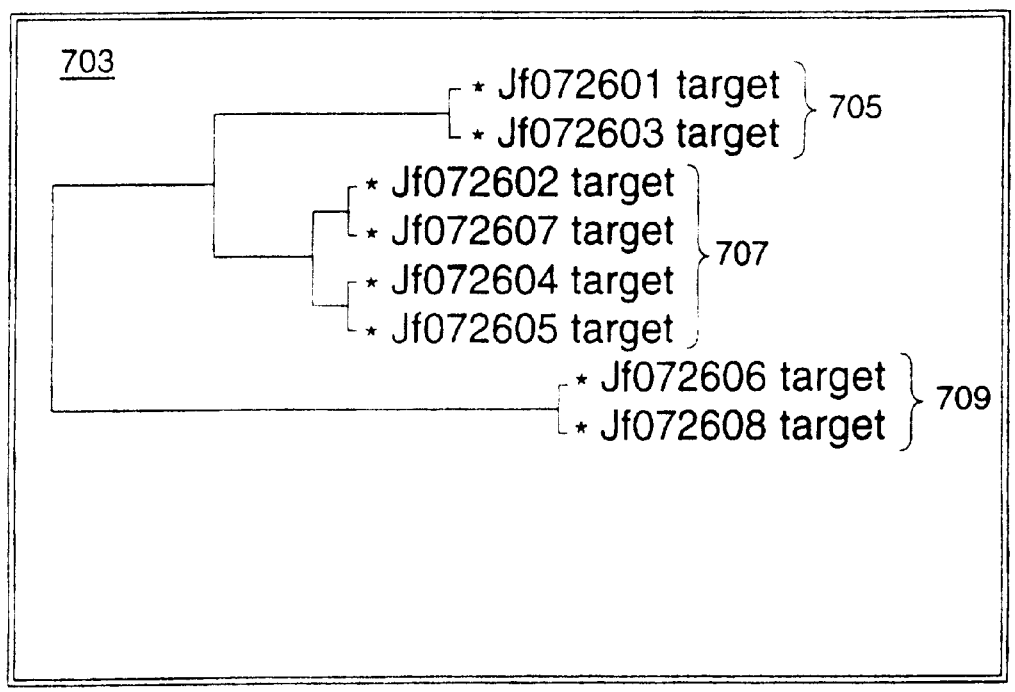
FIG. 12 illustrates a dendrogram indicating that there is likely more than one polymorphism at the base position of interest.

As another example, FIG. 12 illustrates a screen display including a dendrogram indicating that there is likely more than one polymorphism at the base position of interest. A dendrogram 703 shows the clustering of eight sets of hybridization affinity information. A visual inspection of the dendrogram reveals that there appears to be three clusters 705, 707 and 709 where the distance between members of one cluster is much less than the distance between members of other clusters. Since the patterns fall in three clusters, there are likely two polymorphisms at the interrogation position.

With the invention, phenomena that are not obvious through examination of a single hybridization reaction can be detected. Conversely, the number and diversity of probes for recognizing a particular class of phenomena can be reduced. For example, mutations in the BRCA gene are so diverse that constructing a set of probes that would cover every possible polymorphism may be impractical. However, the invention may be utilized to detect such polymorphisms even in the absence of such probes.

In addition, clustering can be utilized to analyze or evaluate the effectiveness of experimental systems, such as genotyping chips, in which useful results are dependent on the detection of a fixed number of highly reproducible classes in the resulting data. In the case of genotyping, one expects three tightly clustered result classes representing homozygous wildtype, homozygous mutant and heterozygote genotypes, respectively. Metrics computed on the hierarchy of patterns generated by a clustering algorithm can provide a quantitative assessment of the specificity and reproducibility of the genotyping process.

While the above is a complete description of preferred embodiments of the invention, various alternatives, modifications, and equivalents may be used. It should be evident that the invention is equally applicable by making appropriate modifications to the embodiments described above. For example, the invention has been described in reference to nucleic acid probes that are synthesized on a chip. However, the invention may be advantageously applied to other monomers (e.g., amino acids and saccharides) and other hybridization techniques including those where the probes are not attached to a substrate. Therefore, the above description should not be taken as limiting the scope of the invention that is defined by the metes and bounds of the appended claims along with their full scope of equivalents.

What is claimed is:

1. A method of detecting differences in sample polymers, comprising:
   inputting a plurality of sets of hybridization affinity information, each set of hybridization affinity information including hybridization affinities between a sample polymer and polymer probes;
   clustering the plurality of sets of hybridization affinity information into a plurality of clusters such that all sets of hybridization affinity information in each cluster are more similar to each other than to the sets of hybridization affinity information in another cluster; and
   analyzing the plurality of clusters to determine a number of clusters, such that the number of clusters indicates if there are differences in the sample polymers.

2. The method of claim 1, wherein the clustering the plurality of sets of hybridization affinity information includes calculating mean linkage clustering of the clusters.

3. The method of claim 2, wherein the mean linkage clustering of the probes utilizes a distance metric for differences between clusters.

4. The method of claim 3, wherein the distance metric is a Euclidean distance or a city-block distance.

5. The method of claim 1, further comprising displaying a tree structure of the plurality of clusters.

6. The method of claim 5, wherein the distance between the clusters varies with the similarity of the clusters.

7. The method of claim 1, wherein the sample polymers include nucleic acids, amino acids or saccharides.

8. A computer program product that detects differences in sample polymers, comprising:
   computer code that receives a plurality of sets of hybridization affinity information, each set of hybridization affinity information including hybridization affinities between a sample polymer and polymer probes;
   computer code that clusters the plurality of sets of hybridization affinity information into a plurality of clusters such that all sets of hybridization affinity information in each cluster are more similar to each other than to the sets of hybridization affinity information in another cluster;
   computer code that analyzes the plurality of clusters to determine a number of clusters, such that the number of clusters indicates if there are differences in the sample polymers; and
   a computer readable medium that stores the computer codes.

9. The computer program product of claim 8, wherein the computer readable medium is selected from the group consisting of floppy disk, tape, flash memory, system memory, hard drive, and a data signal embodied in a carrier wave.

10. A method of detecting polymorphisms in sample nucleic acid sequences, comprising:

inputting a plurality of sets of hybridization affinity information, each set of hybridization affinity information including hybridization affinities between a sample nucleic acid sequence and nucleic acid probes;

hierarchically clustering the plurality of sets of hybridization affinity information into a plurality of clusters such that all sets of hybridization affinity information in each cluster are more similar to each other than to the sets of hybridization affinity information in another cluster; and analyzing the plurality of clusters to determine a number of clusters, such that the number of clusters indicates if there are polymorphisms in the sample polymers.

11. The method of claim 10, wherein the sample nucleic acid sequence and nucleic acid probes include both sense and anti-sense strands.

12. The method of claim 11, wherein the hybridization affinity information includes four hybridization affinities for the sense strands and four hybridization affinities for the anti-sense strands.

13. The method of claim 12, wherein the four hybridization affinities for the sense strands represent hybridization affinities between nucleic acid probes that differ by at least a nucleic acid at an interrogation position.

14. The method of claim 12, wherein the four hybridization affinities for the anti-sense strands represent hybridization affinities between nucleic acid probes that differ by at least a nucleic acid at an interrogation position.

15. The method of claim 10, wherein the polymorphisms include mutations, deletions and insertions at an interrogation position.

16. The method of claim 10, further comprising normalizing the hybridization affinity information for each set.

17. The method of claim 16, wherein the normalizing the hybridization affinity information for each set includes subtracting an average hybridization affinity from the hybridization affinities and dividing each hybridization affinity by a square root of the sum of squares of the hybridization affinities.

18. The method of claim 10, wherein the clustering the plurality of sets of hybridization affinity information includes calculating mean linkage clustering of the clusters.

19. The method of claim 18, wherein the mean linkage clustering of the probes utilizes a distance metric for differences between clusters.

20. The method of claim 19, wherein the distance metric is a Euclidean distance or a city-block distance.

21. The method of claim 10, further comprising displaying a tree structure of the plurality of clusters.

22. The method of claim 21, wherein the distance between the clusters varies with to the similarity of the clusters.

23. A computer program product that detects polymorphisms in sample nucleic acid sequences, comprising:

computer code that receives a plurality of sets of hybridization affinity information, each set of hybridization affinity information including hybridization affinities between a sample nucleic acid sequence and nucleic acid probes;

computer code that hierarchically clusters the plurality of sets of hybridization affinity information into a plurality of clusters such that all sets of hybridization affinity information in each cluster are more similar to each other than to the sets of hybridization affinity information in another cluster;

computer code that analyzes the plurality of clusters to determine a number of clusters, such that the number of clusters indicates if there are polymorphisms in the sample polymers; and a computer readable medium that stores the computer codes.

24. The computer program product of claim 23, wherein the computer readable medium is selected from the group consisting of floppy disk, tape, flash memory, system memory, hard drive, and a data signal embodied in a carrier wave.

25. The computer program product of claim 8, wherein the computer code that clusters the plurality of sets of hybridization affinity information includes computer code that calculates mean linkage clustering of the clusters.

26. The computer program product of claim 25, wherein the mean linkage clustering of the probes utilizes a distance metric for differences between clusters.

27. The computer program product of claim 26, wherein the distance metric is a Euclidean distance or a city-block distance.

28. The computer program product of claim 8, further comprising computer code that displays a tree structure of the plurality of clusters.

29. The computer program product of claim 28, wherein the distance between the clusters varies with the similarity of the clusters.

30. The computer program product of claim 8, wherein the sample polymers include nucleic acids, amino acids or saccharides.

31. The computer program product of claim 23, wherein the sample nucleic acid sequence and nucleic acid probes include both sense and anti-sense strands.

32. The computer program product of claim 31, wherein the hybridization affinity information includes four hybridization affinities for the sense strands and four hybridization affinities for the anti-sense strands.

33. The computer program product of claim 32, wherein the four hybridization affinities for the sense strands represent hybridization affinities between nucleic acid probes that differ by at least a nucleic acid at an interrogation position.

34. The computer program product of claim 32, wherein the four hybridization affinities for the anti-sense strands represent hybridization affinities between nucleic acid probes that differ by at least a nucleic acid at an interrogation position.

35. The computer program product of claim 23, wherein the polymorphisms include mutations, deletions and insertions at an interrogation position.

36. The computer program product of claim 23, further comprising computer code that normalizes the hybridization affinity information for each set.

37. The computer program product of claim 36, wherein the computer code that normalizes the hybridization affinity information for each set includes computer code that subtracts an average hybridization affinity from the hybridization affinities and divides each hybridization affinity by a square root of the sum of squares of the hybridization affinities.

38. The computer program product of claim 23, wherein the computer code that clusters the plurality of sets of hybridization affinity information includes computer code that calculates mean linkage clustering of the clusters.

39. The computer program product of claim 38, wherein the mean linkage clustering of the probes utilizes a distance metric for differences between clusters.

40. The computer program product of claim 39, wherein the distance metric is a Euclidean distance or a city-block distance.

41. The computer program product of claim 23, further comprising computer code that displays a tree structure of the plurality of clusters.

42. The computer program product of claim 41, wherein the distance between the clusters varies with to the similarity of the clusters.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:1:

TTTAATTTTT TTAGGATGTG GGATTTAATT CATCATTGGC          40

(2) INFORMATION FOR SEQ ID NO:2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:2:

TTTAATTTTT TTAGGATGTN GGATTTAATT CATCATTTCC          40

(2) INFORMATION FOR SEQ ID NO:3:

(i) SEQUENCE CHARACTERISTICS:
      (A) LENGTH: 40 base pairs
      (B) TYPE: nucleic acid

```
            (C) STRANDEDNESS: single
            (D) TOPOLOGY: linear (xi) SEQUENCE DESCRIPTION: SEQ ID NO:3:

TTTAATTTTT TTAGNATGTN GGATTTAATT CATCATTTCC                             40

(2) INFORMATION FOR SEQ ID NO:4:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:4:

TTTAATTTTT TTAGNATGTN GNATTTAATT CATCATTTCC                             40

(2) INFORMATION FOR SEQ ID NO:5:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:5:

TTTAATTTTT TTAGNATGTA GNATTTAATT CATCATTTNC                             40

(2) INFORMATION FOR SEQ ID NO:6:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:6:

TTTAATTTTT TTAGGATGTA GGATTTAATT CATCATTNNC                             40
```